(12) United States Patent
Norris

(10) Patent No.: US 8,879,066 B2
(45) Date of Patent: Nov. 4, 2014

(54) TEXTURE ANALYSIS OF A PAINTED SURFACE USING SPECULAR ANGLE DATA

(71) Applicant: PPG Industries Ohio, Inc., Cleveland, OH (US)

(72) Inventor: Alison M. Norris, Avon, OH (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 13/832,116

(22) Filed: Mar. 15, 2013

(65) Prior Publication Data

US 2014/0118736 A1 May 1, 2014

Related U.S. Application Data

(60) Provisional application No. 61/718,729, filed on Oct. 26, 2012.

(51) Int. Cl.
| | |
|---|---|
| *G01N 21/55* | (2014.01) |
| *G01N 21/57* | (2006.01) |
| *G01J 3/50* | (2006.01) |
| *G01N 21/84* | (2006.01) |
| *G01N 21/25* | (2006.01) |

(52) U.S. Cl.
CPC ............... *G01N 21/25* (2013.01); *G01N 21/57* (2013.01); *G01J 3/504* (2013.01); *G01N 21/8422* (2013.01); *G01N 21/55* (2013.01)
USPC ........................................................ 356/445

(58) Field of Classification Search
CPC .............. G01N 21/255; G01N 2021/6484; G01N 21/6486; G01N 21/4738; G01N 2021/4747; G01N 2021/575; G01N 2021/213; G01N 21/211; G01N 2021/4711; G01N 2021/4742; G01N 2021/4771; G01N 21/47; G01N 21/4788
See application file for complete search history.

(56) References Cited

U.S. PATENT DOCUMENTS

| | | | | |
|---|---|---|---|---|
| 4,711,580 A * | 12/1987 | Venable | ...................... | 356/406 |
| 5,231,472 A * | 7/1993 | Marcus et al. | ................ | 356/402 |
| 6,166,814 A * | 12/2000 | Pringle | ......................... | 356/445 |
| 8,606,731 B2 * | 12/2013 | Fujieda et al. | .................. | 706/25 |
| 2005/0169518 A1 * | 8/2005 | Boston et al. | ................. | 382/162 |
| 2006/0245632 A1 | 11/2006 | Nisper et al. | | |
| 2007/0200337 A1 * | 8/2007 | Johnson et al. | ................. | 283/91 |
| 2008/0278723 A1 | 11/2008 | Merchak | | |
| 2009/0015835 A1 | 1/2009 | Balakrishnan et al. | | |
| 2009/0213120 A1 * | 8/2009 | Nisper et al. | .................. | 345/426 |
| 2010/0228511 A1 * | 9/2010 | Chin et al. | ..................... | 702/82 |
| 2011/0282613 A1 * | 11/2011 | Skinner et al. | ................ | 702/104 |

FOREIGN PATENT DOCUMENTS

| | | | |
|---|---|---|---|
| WO | WO 2006/096521 A2 | 9/2006 | |
| WO | WO 2007/096402 A2 | 1/2009 | |

* cited by examiner

*Primary Examiner* — Michael P Stafira
(74) *Attorney, Agent, or Firm* — Jonathan Parks

(57) ABSTRACT

A computer implemented method. The method includes obtaining, using a processor, spectral reflectance data from a spectrophotometric measurement of a target coating on a surface, wherein the measurement was taken at a specular angle, and removing, using the processor, at least a portion of the specular reflectance data that is attributable to a glossy coating of the surface. The method also includes constructing, using the processor, at least one spectral reflectance curve, and identifying, using the processor, at least one type of pigmentation effect of the target coating based at least in part on the at least one spectral reflectance curve.

15 Claims, 4 Drawing Sheets

US 8,879,066 B2

TEXTURE ANALYSIS OF A PAINTED SURFACE USING SPECULAR ANGLE DATA

CROSS REFERENCE TO RELATED APPLICATION

The present application claims priority to U.S. Provisional Patent Application No. 61/718,729, filed Oct. 26, 2012.

FIELD OF THE INVENTION

In various embodiments, the present invention generally relates to a method and apparatus for identifying physical property attributes of cured complex coating (e.g., paint) mixtures using specular angle data retrieved from a spectrophotometer.

BACKGROUND OF THE INVENTION

The specular angle is defined in relation to a spectrophotometer as the angle of reflectance equal and opposite to the angle of incident, illuminant light based on the normal line to the surface coating being measured. The specular angle is also referred to as the gloss angle. By way of example, in conventional handheld spectrophotometers, the specular angle is denoted as "45as0," or 45 aspecular 0, where the incident light is at 45 degrees to the normal of the target and the reflected light data is gathered at 0 degrees from specular or the equal and opposite 45 degrees from normal, thereby specular itself.

Typically, specular angle data is not gathered or reported in spectrophotometer data because there is an assumption that the data at the angle is highly variable due to the extremely high reflectance data received at the angle. Also, because of the very high reflectance data retrieved from the instrumentation, the shape of the reflectance curve of the specular angle always looks the same for every sample, despite the color or gonioeffects of the sample.

Thus, a need exists for systems and methods that utilize specular angle data to characterize the particles that are present in a target coating mixture.

SUMMARY OF THE INVENTION

In various embodiments, the present invention generally relates to a method and apparatus for identifying physical property attributes of cured complex coating (e.g., paint) mixtures using specular angle data retrieved from a spectrophotometer.

In various embodiments, the present invention is directed to computer implemented method. The method includes obtaining, using a processor, spectral reflectance data from a spectrophotometric measurement of a target coating on a surface, wherein the measurement was taken at a specular angle, and removing, using the processor, at least a portion of the specular reflectance data that is attributable to a glossy coating of the surface. The method also includes constructing, using the processor, at least one spectral reflectance curve, and identifying, using the processor, at least one type of pigmentation effect of the target coating based at least in part on the at least one spectral reflectance curve.

In various embodiments, the present invention is directed to a system. The system includes a spectrophotometer and a processor configured to communicate with the spectrophotometer. The processor is programmed to obtain spectral reflectance data from a spectrophotometric measurement of a target coating on a surface, wherein the measurement was taken at a specular angle using the spectrophotometer, and remove at least a portion of the specular reflectance data that is attributable to a glossy coating of the surface. The processor is also programmed to construct at least one spectral reflectance curve, and identify at least one type of pigmentation effect of the target coating based at least in part on the at least one spectral reflectance curve.

In various embodiments, the present invention is directed to an apparatus. The apparatus includes means for obtaining spectral reflectance data from a spectrophotometric measurement of a target coating on a surface, wherein the measurement was taken at a specular angle, and means for removing at least a portion of the specular reflectance data that is attributable to a glossy coating of the surface. The apparatus also includes means for constructing at least one spectral reflectance curve, and means for identifying at least one type of pigmentation effect of the target coating based at least in part on the at least one spectral reflectance curve.

In various embodiments, the present invention is directed to a non-transitory computer readable medium including software for causing a processor to:
  obtain spectral reflectance data from a spectrophotometric measurement of a target coating on a surface, wherein the measurement was taken at a specular angle using the spectrophotometer;
  remove at least a portion of the specular reflectance data that is attributable to a glossy coating of the surface;
  construct at least one spectral reflectance curve; and
  identify at least one type of pigmentation effect of the target coating based at least in part on the at least one spectral reflectance curve.

DETAILED DESCRIPTION OF THE INVENTION

In various aspects, embodiments of the invention include a spectrophotometer and a method that may be used to identify bulk effects that are present in a coating composition on a target sample. Various embodiments of the invention include an apparatus that has a device for capturing information for a target sample and a processor for identifying bulk effects that can be used to produce a paint having a texture that is similar to the target sample. An output device may be used for conveying the bulk effect information to a user.

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a stand alone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Figure 1:
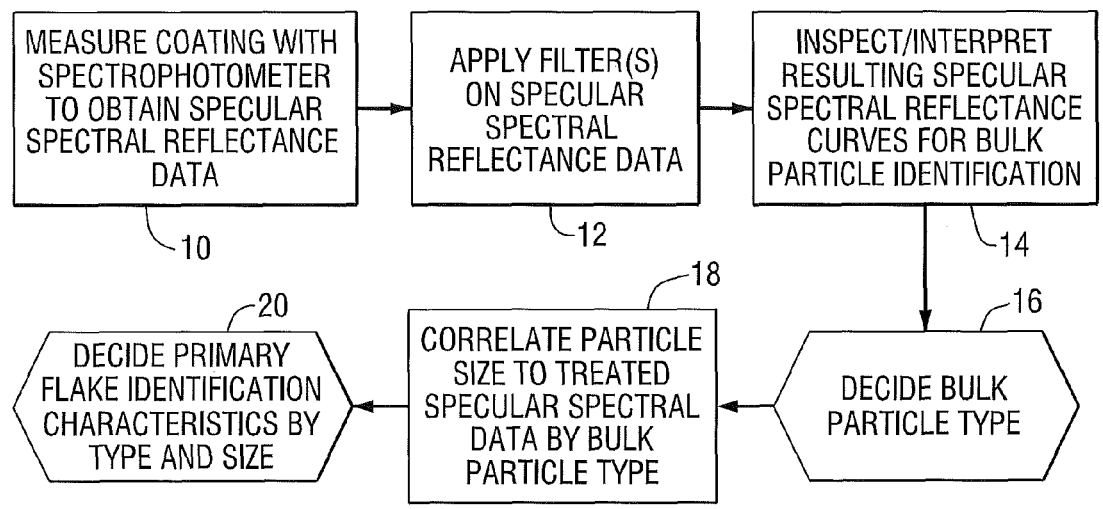
FIG. 1 illustrates a flowchart of an embodiment of a process for identifying particles in a target sample coating mixture.

In various embodiments, specular angle data is used to identify a target coating's composition. The raw (spectral reflectance) data, as it is returned from the instrumentation, does not generally provide enough information about the target coating composition, so the data may be manipulated to obtain satisfactory results. FIG. 1 illustrates a flow diagram of an embodiment of a process that uses specular angle data obtained from a spectrophotometer. In various embodiments, in order to make use of the specular angle data obtained from a spectrophotometer at step 10, the following assumptions may be employed:
  (i) The panel is of a glossy (non-matte) appearance, usually due to the use of a clear coat.
  (ii) The majority of the light reflected at the specular angle is due to the gloss of the surface, or the clear coat.
  (iii) A glossy solid black sample measured on a spectrophotometer will reflect only the light of the gloss from the clear coat and any other light is absorbed at 100% by the black coating.

Embodiments of the present invention transform the raw spectral reflectance data from the specular angle into distinctive, useable information. The resulting information yields a modified spectral reflectance curve (i.e., the curve is modified or treated by removing the specular reflectance that is due to gloss, and is thus a "gloss removed" curve). The spectral reflectance curve can be used on its own for effect identification purposes, and may be used to calculate tristimulus and other colorimetric data and information for analysis purposes.

The process of FIG. 1 proceeds at step 12 where a filter is applied to the specular spectral reflectance data. Using a static, standard measurement of a glossy black surface, the aforementioned assumptions are invoked for the measured reflectance at the specular angle only. By way of example, a glossy black surface may be a solid black paint, coated to opacity, which is then coated with a clear, glossy topcoat or a sample of a polished black glass. It is desirable that the clearcoat match that used on the target coating. In various embodiments, in cases where the clearcoat does not match the clearcoat that is used on the target coating or the clearcoat is unknown, polished black glass may be used, or the process may be completed using multiple glossy black standard measurements and choosing the average of the most closely aligned results. The specular angle reflectance data for the target coating is also measured. The "gloss only" specular reflectance is then subtracted from the target coating's specular reflectance as shown in equation (1) below:

$$R_t(w) - R_s(w) \quad (1)$$

where $R_t$ is the specular spectral reflectance of the target coating at given wavelength w, and $R_s$ is the specular spectral reflectance of the standard black measurement at given wavelength w. The remaining, resulting spectral reflectance curve has now removed the "gloss" component. In various embodiments, the subtraction of the gloss component may be completed using weighting factors on specific or all wavelengths.

Inspecting a plot of the resulting "gloss removed" spectral reflectance curve for the specular angle at step 14 in FIG. 1 allows for classification of the types of pigment contained in the target coating at step 16. The evaluation of the "gloss removed" spectral reflectance curve may include an understanding of the maximum and average magnitudes of "gloss removed" reflectance across all wavelengths and the overall shapes and/or slopes of the entire specular angle spectral reflectance curve.

Figure 2:
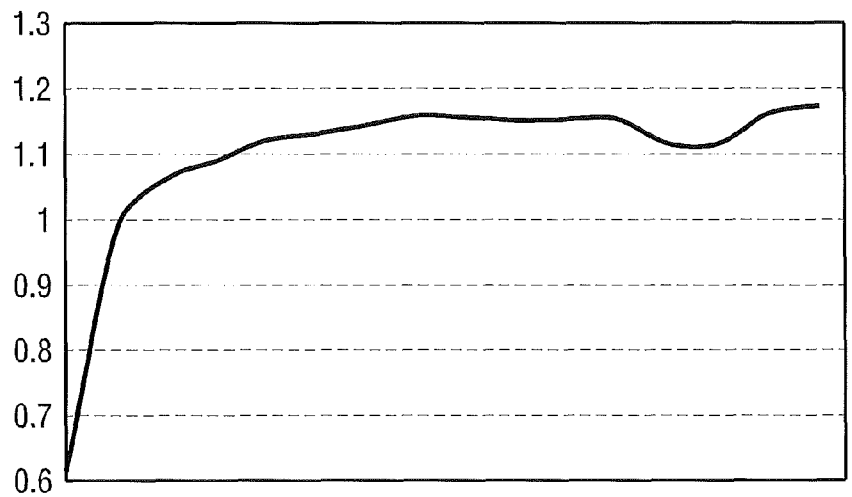
FIGS. 2 through 4 illustrate embodiments of specular angle spectral reflectance curves.
Figure 3:
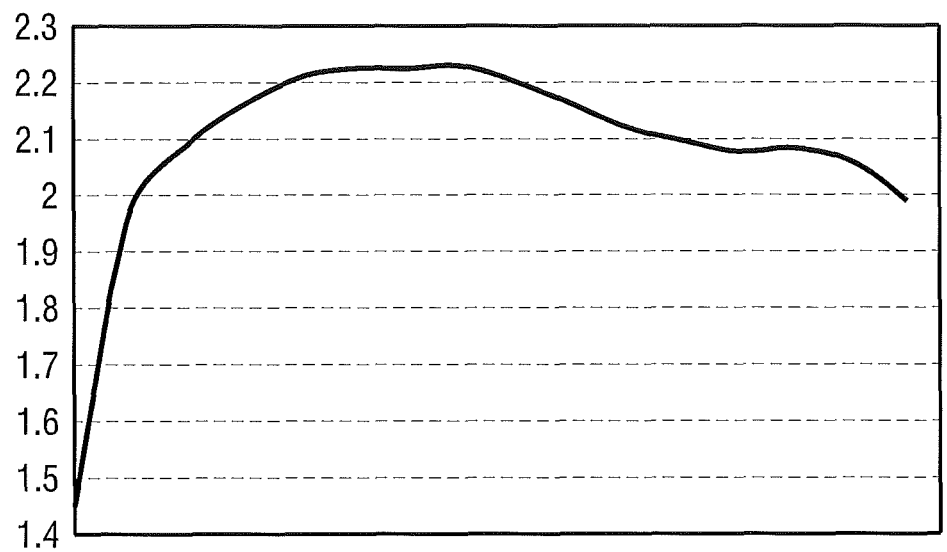
Figure 4:
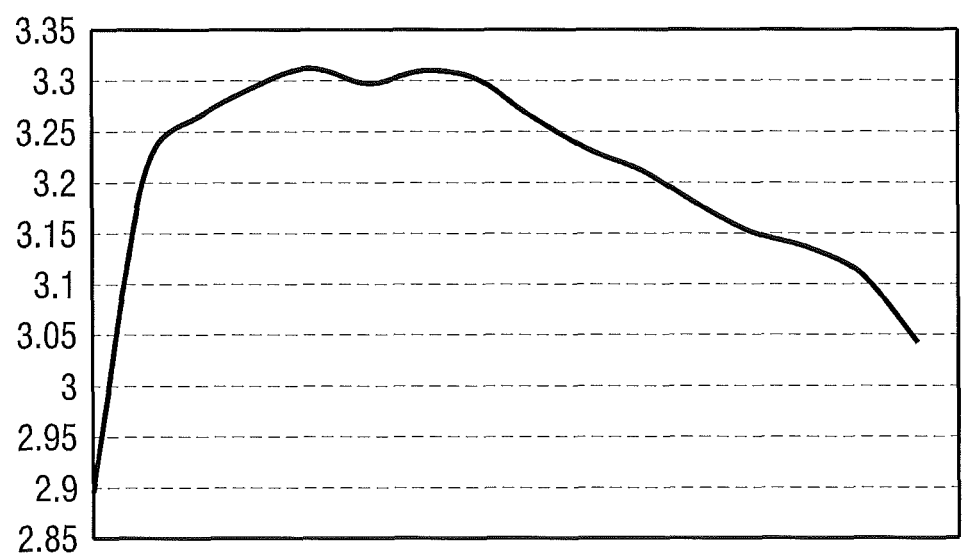

The maximum and average magnitude of reflectance across all measured wavelengths is an indicator of the type of pigmentation contained in the target coating. A specular angle spectral reflectance curve with a maximum and/or average magnitude of approximately 1 or less indicates a high probability of only dispersed pigments in the target coating, meaning the target coating does not include gonioapparent pigments such as aluminums or pearls, as illustrated in FIG. 2. A specular angle spectral reflectance curve with a maximum and/or average magnitude much greater than 1 would indicate a high probability of the use of a gonioapparent pigment, as illustrated in FIG. 3. Furthermore, a maximum and/or average magnitude near 2 indicates a high probability of the use of an aluminum-type pigment, while a maximum and/or average magnitude near or much greater than 3 indicates a high probability of the use of a pearl-type pigment, as illustrated in FIG. 4. FIGS. 2, 3, and 4 are all examples of masstone, single-pigment colors.

The overall shape and/or slopes of the entire specular angle spectral reflectance curve is also indicative of characteristics of the target coating. At maximum and/or average magnitudes of less than 1, the specular angle spectral reflectance curve may be used with standard Kulbelka Munk theory to define which dispersed pigments can be used at concentrations to match the spectral curve. At maximum and/or average magnitudes greater than one, the shape of the entire reflectance curve indicates the color of the primary pearl or aluminum flake in the target coating. The slope of any relatively straight line reflectance curves may be correlated to the flake size of the primary gonioapparent pigment in the target coating.

The treated specular spectral reflectance data may be empirically correlated to known characteristics in order to identify primary flake types in complex coating mixtures. Statistical data may be calculated from the treated specular spectral reflectance, such as sum, average, standard deviation, etc., or new colorimetric information may be calculated from the treated specular spectral reflectance data. The new data points are then calculated from an empirical dataset, representative of the expected mixtures and colors that will need to be handled in everyday situations. At step 18 of FIG. 1, the empirical data set is used to create a predictive correlation: $y=f(x)$, where y represents the desired characteristic for identification (i.e., primary flake type is solid, pearl, or aluminum), and $f(x)$ is some function of x's, where x is one or multiple variables using the statistical data from the treated specular spectral reflectance or the newly calculated colorimetric information from the treated specular spectral reflectance. The resulting function can be linear or non-linear as defined by the empirical data set.

Also, the treated specular spectral reflectance data may be compared to other angular spectral data as described in U.S. patent application Ser. No. 13/832,088 entitled "Multi-Angular Color, Opacity, Pigment Characterization, and Texture Analysis of a Painted Surface Via Visual And/Or Instrumental Techniques," filed on even date herewith, and which is incorporated herein by reference.

The rough average particle size of the primary effect flake may be determined from the data at the specular angle. The prediction may be useful for aluminum flakes and correlations may be achieved in masstone aluminum situations. However, once the generic flake type has been identified using embodiments of the process described herein, any flake type may be correlated to flake size using data from the specular angle.

In order to identify generic flake size, an empirical data set may be employed to create a correlation between the specular data and the flake size. The empirical data set may be varied both in color space as well as flake type and may be segmented by primary flake type. The flake size information for each data point within the data set, or segmented data sets, is fixed. This can be achieved in one of several ways. By way of example, embodiments of methods include: (i) the use of qualitative categorical data such as "Fine," "Medium," or "Coarse," (ii) the use of quantitative continuous numerical data such as D10, D50, D90, or (iii) the use of quantitative or qualitative ordinal data such as ranked flake size buckets where one side of the scale indicates a small flake size which gradually increases to the other side of the scale, which indicates a large flake size. For each data point within the data set, the flake size may be attributable to the primary flake within the coating. Then, the specular angle spectral reflectance data may be statistically gathered into a single result for each data point. In one embodiment a simple sum across all wavelengths is used, as per the following equation (2):

$$\Sigma_{w=400-700} R(w) \quad (2)$$

Figure 5:
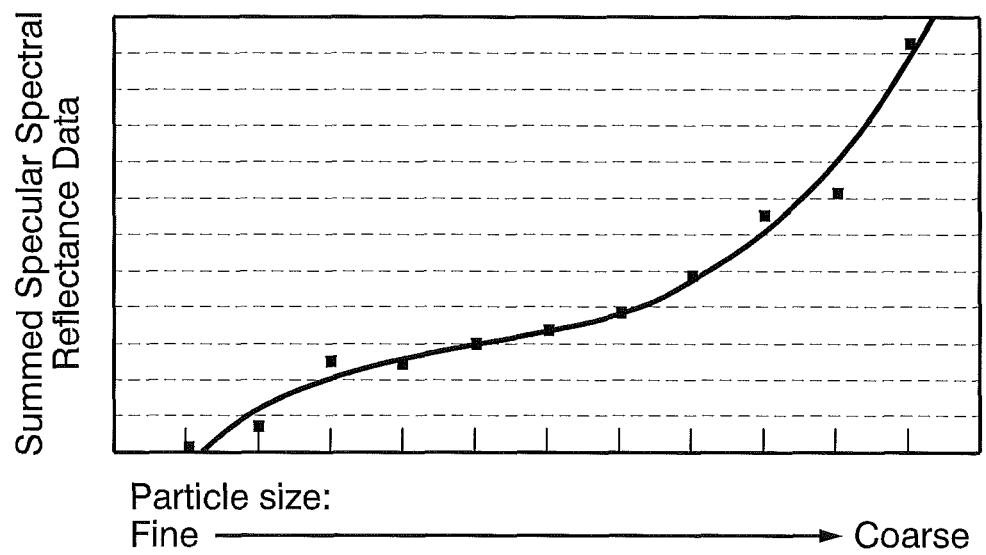
FIG. 5 illustrates an embodiment of a graph of a correlation function for aluminum as a coating effect.

Using a plurality of data results for each data point within the data set, a correlation can be achieved, $y=f(x)$, where the flake size (y) is a function of the data from the specular angle (x). The correlation may be non-linear, however in various embodiments it may be desirable to not over-fit the data points. In various embodiments, the $R^2$ of the correlation may be improved upon by including additional known variables, such as angular colorimetric data, maximum treated specular spectral reflectance, etc. The process may be repeated for each segmented set of the original data set until there is a correlation per primary flake type. In various embodiments, correlations may overlap or be similar to one another, thus allowing for interpolation between correlations, if desired. An example of a resulting correlation for aluminums is illustrated in FIG. 5.

Once the empirical data set has determined the correlations in various embodiments, at step 20 in FIG. 1 the new equation is applied to data gathered from an unknown coating with a known/identified primary flake type. This information is obtained by calculating the single result specular angle spectral reflectance data point for the unknown coating and substituting it, along with any other necessary information for the correlation, as the variables in the $y=f(x)$ correlation. The resulting flake size, y, is returned in the same format as derived from the original empirical data set.

In various embodiments, in order to understand the effect of flake orientation altering components, such as fumed silica, a similar approach may be taken wherein the empirical data set is divided as to containing or not containing a flake orientation altering component, as well as the percentage of inclusion within the total formula.

Figure 6:
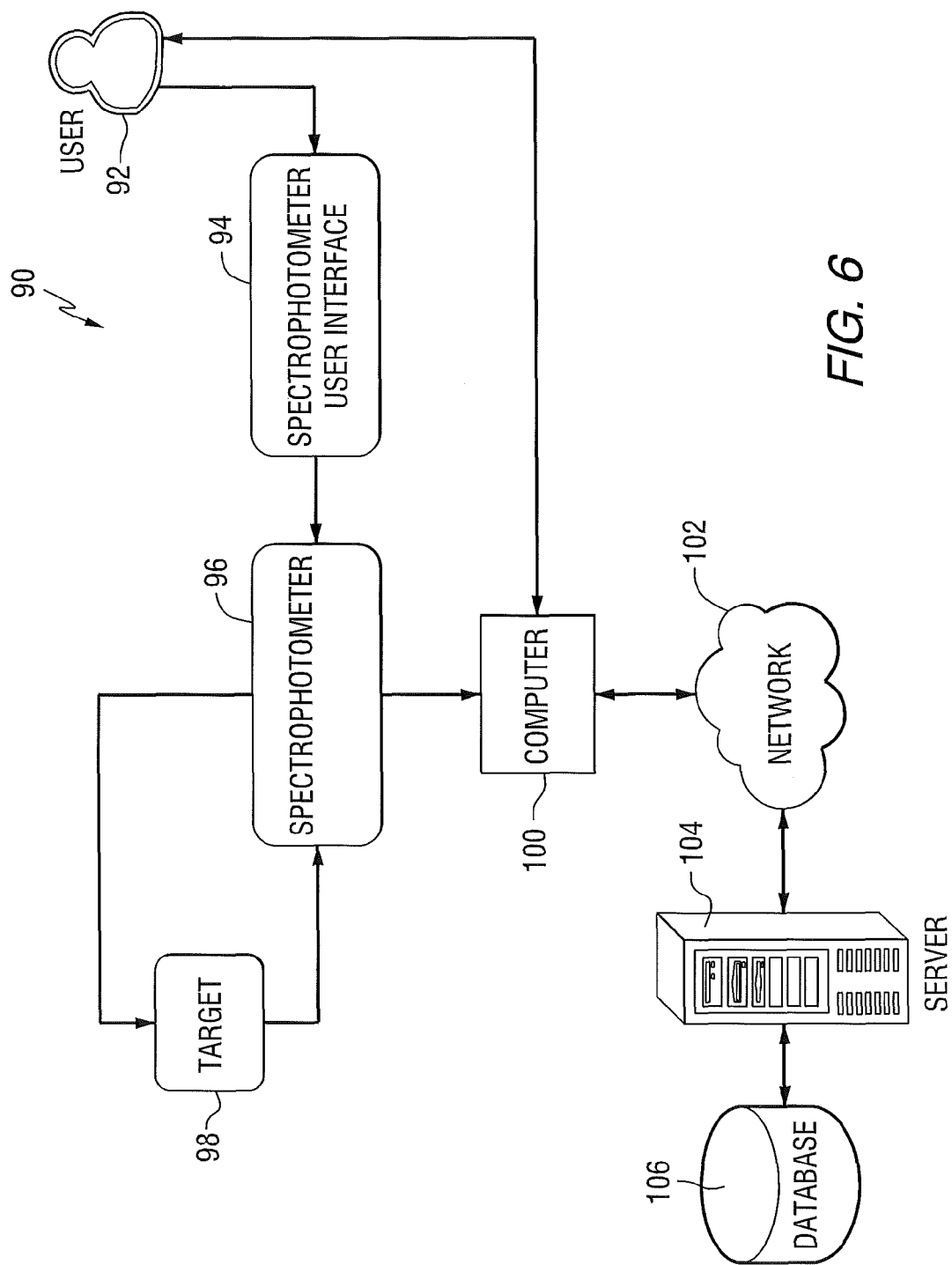
FIG. 6 illustrates an embodiment of a system which may be used to identify physical property attributes of a coating mixture of a target sample.

FIG. 6 illustrates an embodiment of a system 90 which may be used to identify physical property attributes of a coating mixture of a target sample. A user 92 may utilize a user interface 94, such as a graphical user interface, to operate a spectrophotometer 96 to measure the properties of a target sample 98. The data from the spectrophotometer 96 may be transferred to a computer 100, such as a personal computer, a mobile device, or any type of processor. The computer 100 may be in communication, via a network 102, with a server 104. The network 102 may be any type of network, such as the Internet, a local area network, an intranet, or a wireless network. The server 104 is in communication with a database 106 that may store the data and information that is used by the methods of embodiments of the present invention for comparison purposes. Various steps of the methods of embodiments of the present invention may be performed by the computer 100 and/or the server 106.

In another aspect, the invention may be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

What is claimed is:

1. A computer implemented method, comprising:
    obtaining, using a processor, spectral reflectance data from a spectrophotometric measurement of a target coating on a surface, wherein the measurement was taken at a specular angle;
    removing, using the processor, at least a portion of the spectral reflectance data that is attributable to a glossy coating of the surface such that the remaining spectral reflectance data is attributable to at least one type of pigmentation effect of the target coating;
    constructing, using the processor, at least one spectral reflectance curve from the remaining spectral reflectance data; and
    identifying, using the processor, the at least one type of pigmentation effect of the target coating based at least in part on the at least one spectral reflectance curve.

2. The method of claim 1, wherein identifying at least one type of pigmentation effect includes identifying at least one type of pigmentation effect based on a reflectance value of the at least one spectral reflectance curve.

3. The method of claim 2, wherein identifying at least one type of pigmentation effect based on a reflectance value of the at least one spectral reflectance curve includes identifying at least one type of pigmentation effect based on a maximum reflectance value of the at least one spectral reflectance curve across a plurality of wavelengths.

4. The method of claim 2, wherein identifying at least one type of pigmentation effect based on a reflectance value of the at least one spectral reflectance curve includes identifying at least one type of pigmentation effect based on an average reflectance value of the at least one spectral reflectance curve across a plurality of wavelengths.

5. The method of claim 2, wherein identifying at least one type of pigmentation effect based on a reflectance value of the at least one spectral reflectance curve includes identifying at least one type of pigmentation effect based on a slope of the at least one spectral reflectance curve.

6. The method of claim 2, wherein identifying at least one type of pigmentation effect based on a reflectance value of the at least one spectral reflectance curve includes identifying at least one type of pigmentation effect based on a shape of the at least one spectral reflectance curve.

7. The method of claim 1, further comprising calculating tristimulus data based on the at least one spectral reflectance curve.

8. A system, comprising:
- a spectrophotometer; and
- a processor configured to communicate with the spectrophotometer and programmed to:
  - obtain spectral reflectance data from a spectrophotometric measurement of a target coating on a surface, wherein the measurement was taken at a specular angle using the spectrophotometer;
  - remove at least a portion of the spectral reflectance data that is attributable to a glossy coating of the surface such that the remaining spectral reflectance data is attributable to at least one type of pigmentation effect of the target coating;
  - construct at least one spectral reflectance curve from the remaining spectral reflectance data; and
  - identify the at least one type of pigmentation effect of the target coating based at least in part on the at least one spectral reflectance curve.

9. The system of claim 8, further comprising a database in communication with the processor.

10. The system of claim 8, further comprising a user interface in communication with the spectrophotometer.

11. The system of claim 8, wherein the processor is configured to identify the at least one type of pigmentation effect by identifying at least one type of pigmentation effect based on a reflectance value of the at least one spectral reflectance curve.

12. An apparatus, comprising:
- means for obtaining spectral reflectance data from a spectrophotometric measurement of a target coating on a surface, wherein the measurement was taken at a specular angle;
- means for removing at least a portion of the spectral reflectance data that is attributable to a glossy coating of the surface such that the remaining spectral reflectance data is attributable to at least one type of pigmentation effect of the target coating;
- means for constructing at least one spectral reflectance curve from the remaining spectral reflectance data; and
- means for identifying the at least one type of pigmentation effect of the target coating based at least in part on the at least one spectral reflectance curve.

13. The apparatus of claim 12, wherein the means for identifying at least one type of pigmentation effect includes means for identifying at least one type of pigmentation effect based on a reflectance value of the at least one spectral reflectance curve.

14. A non-transitory computer readable medium including software for causing a processor to:
- obtain spectral reflectance data from a spectrophotometric measurement of a target coating on a surface, wherein the measurement was taken at a specular angle using the spectrophotometer;
- remove at least a portion of the spectral reflectance data that is attributable to a glossy coating of the surface such that the remaining spectral reflectance data is attributable to at least one type of pigmentation effect of the target coating;
- construct at least one spectral reflectance curve from the remaining spectral reflectance data; and
- identify the at least one type of pigmentation effect of the target coating based at least in part on the at least one spectral reflectance curve.

15. The computer readable medium of claim 14, further comprising software for causing the processor to identify at least one type of pigmentation effect based on a reflectance value of the at least one spectral reflectance curve.

* * * * *